(12) United States Patent
Tulenko

(10) Patent No.: US 9,827,026 B1
(45) Date of Patent: Nov. 28, 2017

(54) NUSS PROCEDURE AID

(71) Applicant: ALLSCRIPTS SOFTWARE, LLC, Chicago, IL (US)

(72) Inventor: Alexander Tulenko, Wake Forest, NC (US)

(73) Assignee: ALLSCRIPTS SOFTWARE, LLC, Chicago, IL (US)

( * ) Notice: Subject to any disclaimer, the term of this patent is extended or adjusted under 35 U.S.C. 154(b) by 537 days.

(21) Appl. No.: 14/502,834

(22) Filed: Sep. 30, 2014

(51) Int. Cl.
*A61B 17/80* (2006.01)

(52) U.S. Cl.
CPC .......... *A61B 17/80* (2013.01); *A61B 17/8076* (2013.01)

(58) Field of Classification Search
CPC ....... A61B 17/80–17/809; A61B 17/82; A61B 17/823
USPC .............. 606/70, 71, 280–299, 905; 128/898
See application file for complete search history.

(56) References Cited

U.S. PATENT DOCUMENTS

| | | | | |
|---|---|---|---|---|
| 6,024,759 A * | 2/2000 | Nuss | ...................... | A61B 17/68 606/237 |
| 6,569,166 B2 * | 5/2003 | Gonzalez | ........... | A61B 17/8076 606/281 |
| 7,052,499 B2 * | 5/2006 | Steger | ................ | A61B 17/8047 606/280 |
| 7,156,847 B2 * | 1/2007 | Abramson | ......... | A61B 17/8076 606/60 |
| 8,043,290 B2 * | 10/2011 | Harrison | ................ | A61B 17/66 606/60 |
| 8,142,454 B2 * | 3/2012 | Harrison | ............ | A61B 17/0483 606/153 |
| 8,221,421 B2 * | 7/2012 | Hearn | ................ | A61B 17/8009 606/282 |
| 8,428,890 B2 * | 4/2013 | Bawab | ................. | G01B 21/047 702/121 |
| 8,439,915 B2 * | 5/2013 | Harrison | ............ | A61B 17/0483 606/105 |
| 8,460,345 B2 * | 6/2013 | Steger | .................... | A61B 17/80 606/280 |
| 8,715,285 B2 * | 5/2014 | Lewis | ................ | A61B 17/8076 606/71 |
| 8,777,952 B2 * | 7/2014 | Bardajui Pascual | .............. | A61B 17/8076 606/105 |
| 8,795,342 B2 * | 8/2014 | Reisberg | ............ | A61B 17/8076 606/101 |
| 8,876,823 B2 * | 11/2014 | Li | ...................... | A61B 17/8076 606/70 |

(Continued)

Primary Examiner — Eric S Gibson
(74) Attorney, Agent, or Firm — Tillman Wright, PLLC; Chad D. Tillman; Jeremy C. Doerre

(57) ABSTRACT

A method for treating pectus excavatum includes making an incision in the chest of a patient, inserting, via the incision, a device comprising a sensor configured to measure force at a face disposed proximate a first end of the device, manipulating the device such that the face of the device engages a sternum of the patient, displaying, on the electronic display of the device, measurement data based on a reading taken by the sensor during the engagement of the face of the device with the sternum of the patient, and determining, based on the displayed measurement data, a number of bars to install in the patient's chest, and inserting, via one or more incisions, the determined number of bars into the patient's chest in such a manner as to push out the patient's sternum and maintain the patient's sternum in a pushed out condition.

20 Claims, 5 Drawing Sheets

(56) References Cited

U.S. PATENT DOCUMENTS

| | | | | |
|---|---|---|---|---|
| 8,876,824 B2* | 11/2014 | Hearn | A61B 17/8009 | 606/71 |
| 8,915,915 B2* | 12/2014 | Harrison | A61B 17/7016 | 606/60 |
| 9,138,272 B2* | 9/2015 | Roman | A61B 17/8076 | |
| 9,314,285 B2* | 4/2016 | Reisberg | A61B 17/823 | |
| 9,339,388 B2* | 5/2016 | Dartevelle | A61B 17/8076 | |
| 9,668,792 B2* | 6/2017 | Roman | A61B 17/8076 | |
| 2004/0117016 A1* | 6/2004 | Abramson | A61B 17/8076 | 623/16.11 |
| 2006/0058786 A1* | 3/2006 | Kim | A61B 17/8076 | 606/60 |
| 2006/0271107 A1* | 11/2006 | Harrison | A61B 17/0483 | 606/237 |
| 2007/0276378 A1* | 11/2007 | Harrison | A61B 17/0483 | 606/309 |
| 2008/0082101 A1* | 4/2008 | Reisberg | A61B 17/8076 | 606/60 |
| 2009/0048618 A1* | 2/2009 | Harrison | A61B 17/0483 | 606/153 |
| 2010/0114103 A1* | 5/2010 | Harrison | A61B 17/7016 | 606/90 |
| 2010/0211331 A1* | 8/2010 | Bawab | G01B 21/047 | 702/43 |
| 2010/0256691 A1* | 10/2010 | Park | A61B 17/8076 | 606/330 |
| 2011/0166612 A1* | 7/2011 | Bardaj Pascual | A61B 17/8076 | 606/86 R |
| 2011/0208255 A1* | 8/2011 | Su | A61B 17/8076 | 606/86 R |
| 2012/0130371 A1* | 5/2012 | Li | A61B 17/8076 | 606/70 |
| 2014/0128868 A1* | 5/2014 | Harrison | A61B 17/7016 | 606/60 |
| 2014/0163691 A1* | 6/2014 | Dartevelle | A61B 17/8076 | 623/23.53 |
| 2014/0350613 A1* | 11/2014 | Bardaj Pascual | A61B 17/8076 | 606/86 R |
| 2014/0358150 A1* | 12/2014 | Kaufman | A61B 17/025 | 606/90 |
| 2015/0134009 A1* | 5/2015 | Licht | A61B 17/8076 | 606/281 |
| 2015/0196396 A1* | 7/2015 | Thomas | A61B 17/707 | 623/23.47 |

* cited by examiner

NUSS PROCEDURE AID

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention generally relates to a surgical tool.

Pectus excavatum is a condition involving a congenital deformity of the anterior wall of the chest which results in a hollowed-in or sunken chest. In 1987, Dr. Donald Nuss invented a procedure for treating pectus excavatum which involves inserting one or more concave stainless steel bars under the sternum of a patient via one or more incisions in the side of the chest. These bars are then "flipped", causing the sternum to "pop out".

These bars are then left in the patient for several years while the sternum reforms to its new position. Generally, the process involves using one to three bars inside of the patient's chest to hold out the sternum, but sometimes when an insufficient number of bars are used inside of a patient, the bars fail and the patient's sternum pushes back into the patient's chest cavity. Traditionally, a doctor preforming the procedure has to judge how many bars will be needed based on factors such as a patient's age and the resistance of the sternum they feel when installing bars.

Needs exist for improvement in systems, methods, and apparatus for use in correcting pectus excavatum. These, and other needs, are addressed by one or more aspects of the present invention.

SUMMARY OF THE INVENTION

The present invention includes many aspects and features. Moreover, while many aspects and features relate to, and are described in, the context of treating pectus excavatum, the present invention is not limited to use only in this context, as will become apparent from the following detailed descriptions of aspects, features, and one or more embodiments of the present invention.

Accordingly, one aspect of the present invention relates to a method comprising making an incision in the chest of a patient who has been diagnosed with pectus excavatum; inserting, via the incision, a device comprising a sensor configured to measure force at a face disposed proximate a first end of the device, a handle disposed at a second, opposite end of the device, and an electronic display disposed at the handle, the electronic display being configured to display measurement information based on readings taken by the sensor; manipulating the device such that the face of the device engages a sternum of the patient; displaying, on the electronic display of the device, measurement data based on a reading taken by the sensor during the engagement of the face of the device with the sternum of the patient; determining, based on the displayed measurement data, a number of bars to install in the patient's chest; inserting, via one or more incisions, the determined number of bars into the patient's chest in such a manner as to push out the patient's sternum and maintain the patient's sternum in a pushed out condition.

In a feature of this aspect, the step of determining a number of bars to install in the patient's chest comprises determining the number utilizing software configured to do so.

In a feature of this aspect, the sensor comprises a pressure sensor.

In a feature of this aspect, displaying measurement data comprises displaying a measurement of force in Newtons.

In a feature of this aspect, displaying measurement data comprises displaying a measurement in pounds.

In a feature of this aspect, displaying measurement data comprises displaying a measurement in kilograms.

In a feature of this aspect, the handle comprises a non-absorbent material.

In a feature of this aspect, the device is around two feet long.

In a feature of this aspect, determining a number of bars to install comprises determining that two bars should be installed.

In a feature of this aspect, determining a number of bars to install comprises determining that three bars should be installed.

Another aspect relates to a method comprising making an incision in the chest of a patient who has been diagnosed with pectus excavatum; inserting, via the incision, a device comprising a sensor configured to measure force at a face disposed proximate a first end of the device, a handle disposed at a second, opposite end of the device, and a communication interface configured to communicate data based on sensor readings; manipulating the device such that the face of the device engages a sternum of the patient; communicating, from the device via the communication interface, measurement data based on a reading taken by the sensor during the engagement of the face of the device with the sternum of the patient; determining, based on the communicated measurement data, a number of bars to install in the patient's chest; inserting, via one or more incisions, the determined number of bars into the patient's chest in such a manner as to push out the patient's sternum and maintain the patient's sternum in a pushed out condition.

In a feature of this aspect, the step of determining a number of bars to install in the patient's chest comprises determining the number utilizing software configured to do so.

In a feature of this aspect, the sensor comprises a pressure sensor.

In a feature of this aspect, the handle comprises a non-absorbent material.

In a feature of this aspect, the device is around two feet long.

In a feature of this aspect, determining a number of bars to install comprises determining that two bars should be installed.

In a feature of this aspect, determining a number of bars to install comprises determining that three bars should be installed.

In a feature of this aspect, the communication interface comprises a wireless communication interface.

In a feature of this aspect, the communication interface comprises a wired communication interface.

Another aspect relates to a method comprising making an incision in the chest of a patient who has been diagnosed with pectus excavatum; inserting, via the incision, a device comprising a sensor configured to measure force at a face disposed proximate a first end of the device, a handle disposed at a second, opposite end of the device, and an electronic display disposed at the handle; manipulating the device such that the face of the device engages a sternum of the patient; determining, at the device based on a reading taken by the sensor during the engagement of the face of the device with the sternum of the patient, a number of bars to install in the patient's chest; displaying, via the electronic display, the determined number of bars; inserting, via one or more incisions, the determined number of bars into the patient's chest in such a manner as to push out the patient's sternum and maintain the patient's sternum in a pushed out condition.

Another aspect relates to a device for use in determining how many bars to insert into a patient's chest to push out his or her sternum.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings, wherein the same elements are referred to with the same reference numerals, and wherein.

DETAILED DESCRIPTION

Figure 1:
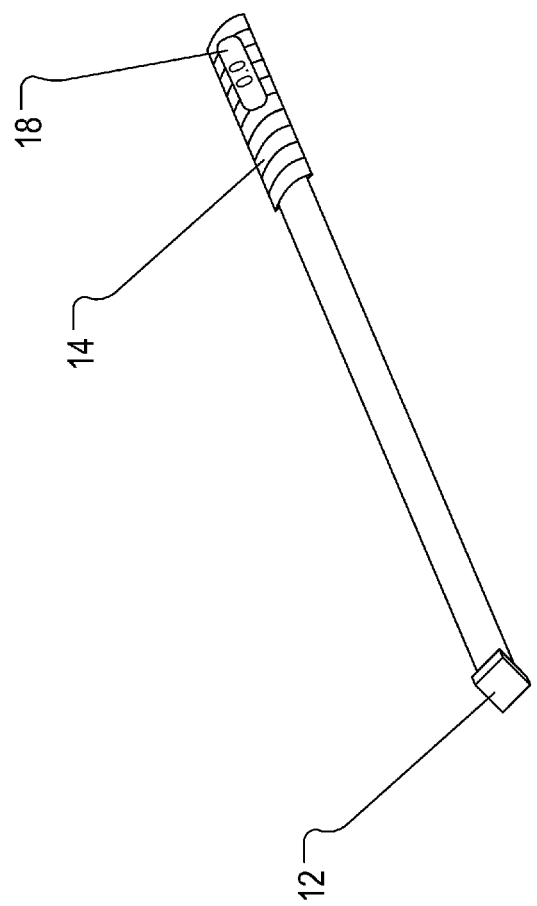
FIGS. 1-5 illustrate exemplary devices in accordance with preferred implementations.

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention in any claim of a patent issuing here from, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the issued claim(s) rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. §112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the present invention are next described. The following description of one or more preferred embodiments is merely exemplary in nature and is in no way intended to limit the invention, its implementations, or uses.

As described above, in the Nuss procedure, one or more bars are inserted inside of a patient's chest to hold out the sternum, but sometimes when an insufficient number of bars are used inside of a patient, the bars fail and the patient's sternum pushes back into the patient's chest cavity.

One or more preferred implementations relate to a tool for use in measuring the force required to push out a patient's sternum so as to inform a decision as to how many bars to utilize.

In accordance with one or more preferred implementations, a device comprises a small rod with a handle allowing it to be firmly gripped. Preferably, the device comprises metal or other strong material to resist bending when used to the push the inside of a patient's sternum. The device preferably includes, at the end of the rod opposite the handle, a sensor (such as a pressure sensor) installed with a face configured for engagement with and pressing on the inside of a patient's sternum. The device preferably further includes, at or proximate the handle, a display, such as an electronic display, configured to display the force (e.g. measured in Newtons) or mass (e.g. measured in pounds or kilograms) measured by the pressure sensor.

Preferably, the handle comprises a material configured to provide a firm grip to a medical practitioner but that is non-absorbent to facilitate use during surgery. In one or more preferred implementations, a device is around two feet long so as to allow for insertion into a patient in a manner such that the sensor at one end of the device can engage the center of a patient's sternum.

In one or more preferred implementations, in addition to having a display, or alternatively, a device includes one or more wired or wireless interfaces configured to allow the device to exchange data with another electronic device, e.g. communicate readings to a computer or mobile electronic device. This might include, for example, via a WiFi or Bluetooth connection.

In one or more preferred implementations, software at a computer or other electronic device is configured to utilize data obtained from a device to determine how many bars to insert into a patient's chest. In one or more preferred implementations, a device itself is configured to determine how many bars to utilize and outputs that information on a display of the device, either in addition to measurement information, or in place thereof.

FIG. 1 illustrates an exemplary device 10 in accordance with one or more preferred implementations. The device 10 includes a sensor disposed at a face 12 proximate one end of the device 10, and a handle 14 at a second, opposite end of the device 10. The device further includes an electronic display 18 configured to display reading data from the sensor.

Figure 2:
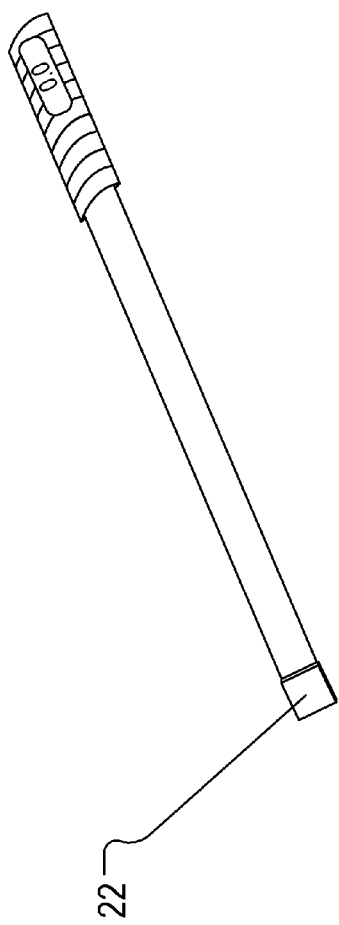

Although the device 10 is illustrated as including a sensor disposed at an end face 12, in one or more preferred implementations, as illustrated in FIG. 2, a device 20 includes a sensor disposed at a face 22 extending from a lengthwise extent of the device 20.

Figure 3:
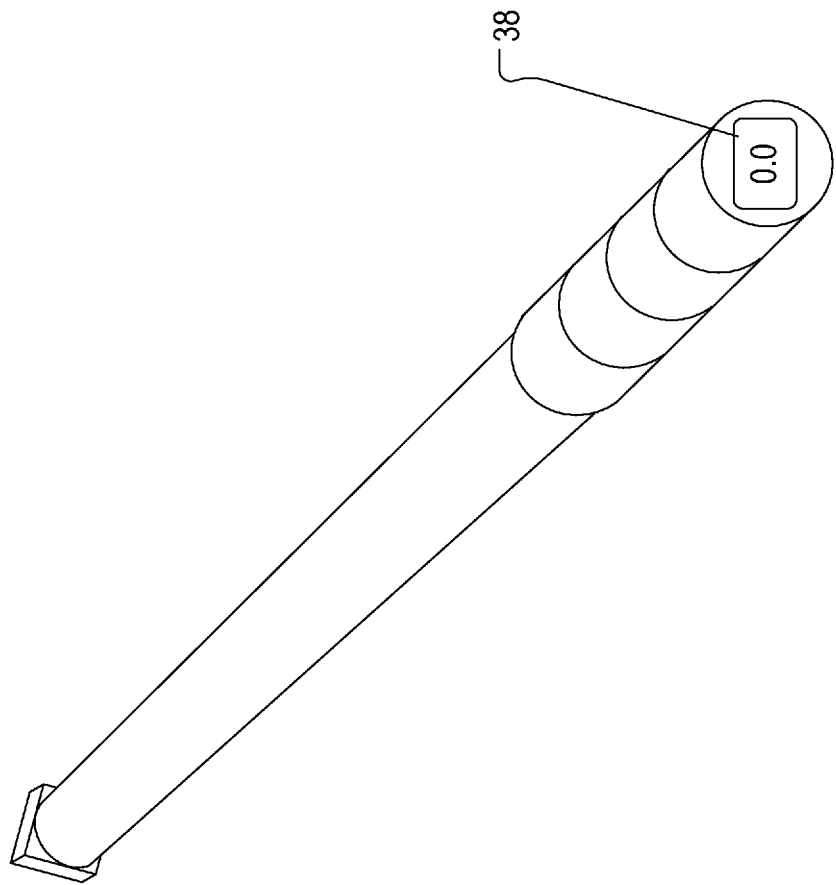

Similarly, although the device 10 is illustrated as including a display 18 disposed along a lengthwise extent of the handle 14, in one or more preferred implementations, as illustrated in FIG. 3, a device 30 includes a display 38 disposed at an end of the device 30.

Figure 4:
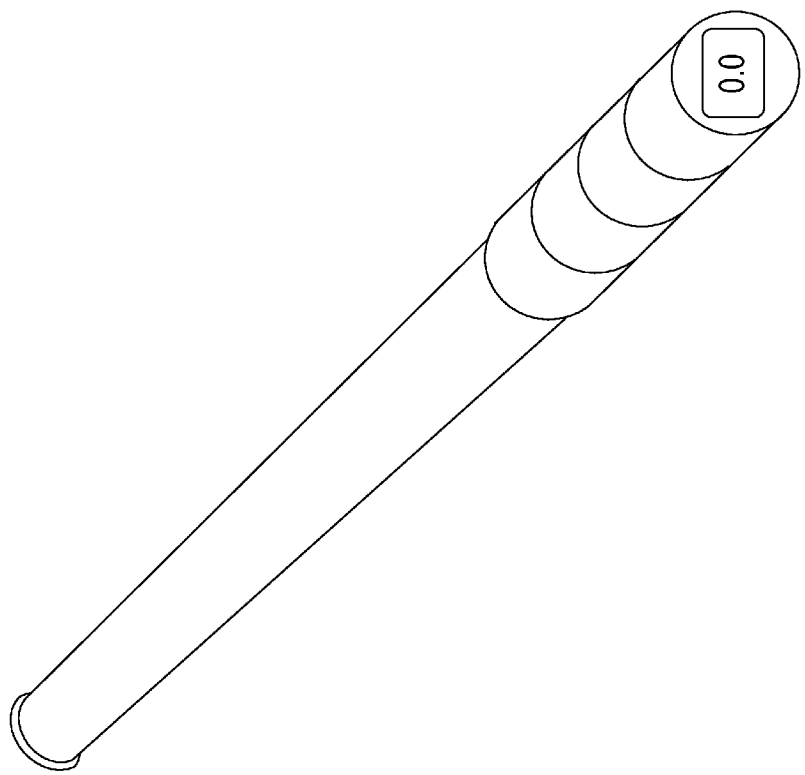
Figure 5:
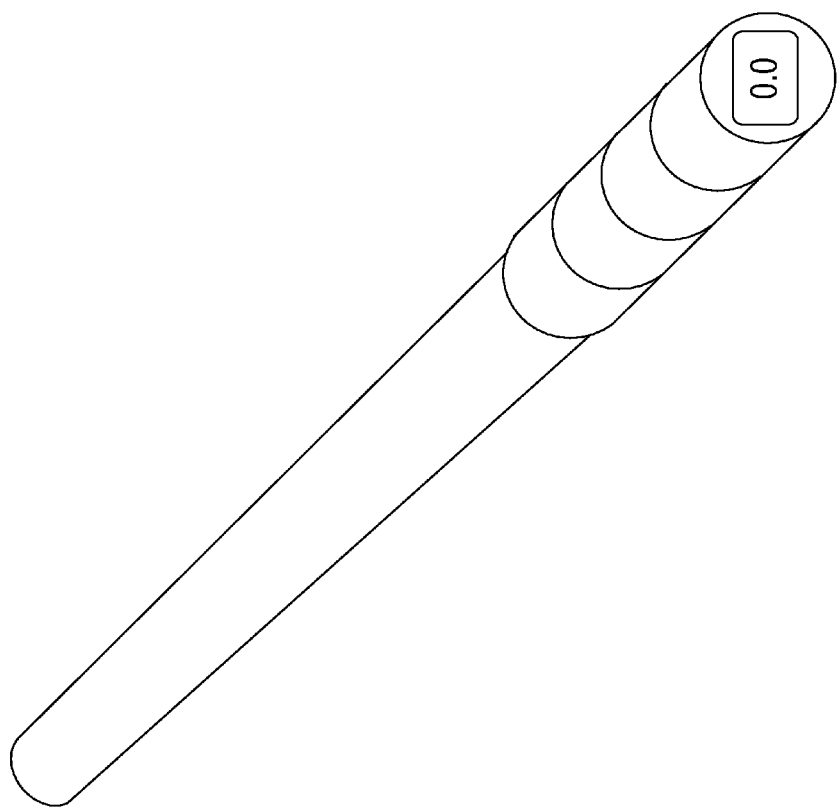

Further, although the devices 10,20,30 are illustrated as including a rectangular face at which a sensor is disposed, this is merely exemplary in nature, and other types of faces may be provided, as illustrated, for example, in FIG. 4 (illustrating exemplary device 40) and FIG. 5 (illustrating exemplary device 50).

In general, it will be appreciated that the illustrations in the figures are illustrations of exemplary devices, and that devices in accordance with various preferred implementations may take various shapes and sizes.

In accordance with one or more preferred implementations, a device including a sensor is configured to measure a force associated with pushing out a patient's sternum. Preferably, the device is inserted into a patient's chest via an incision, and a face of the device engages the patient's sternum so as to obtain a force or resistance measurement associated with the patient's sternum. This measurement is either displayed on an electronic display of the device, or communicated to another electronic device (e.g. via wireless or wired communications). This measurement is utilized to determine a number of bars necessary to insert in accordance with the Nuss procedure to support the patient's sternum, and a surgeon inserts the determined number of bars.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A method comprising:
    (a) making an incision in the chest of a patient who has been diagnosed with pectus excavatum;
    (b) inserting, via the incision, a device comprising
        (i) a sensor configured to measure force at a face disposed proximate a first end of the device,
        (ii) a handle disposed at a second, opposite end of the device, and
        (iii) an electronic display disposed at the handle, the electronic display being configured to display measurement information based on readings taken by the sensor;
    (c) manipulating the device such that the face of the device engages a sternum of the patient;
    (d) displaying, on the electronic display of the device, measurement data based on a reading taken by the sensor during the engagement of the face of the device with the sternum of the patient;
    (e) determining, based on the displayed measurement data, a number of bars to install in the patient's chest; and
    (f) inserting, via one or more incisions, the determined number of bars into the patient's chest in such a manner as to push out the patient's sternum and maintain the patient's sternum in a pushed out condition.

2. The method of claim 1, wherein the step of determining a number of bars to install in the patient's chest comprises determining the number utilizing software configured to do so.

3. The method of claim 1, wherein the sensor comprises a pressure sensor.

4. The method of claim 1, wherein displaying measurement data comprises displaying a measurement of force in Newtons.

5. The method of claim 1, wherein displaying measurement data comprises displaying a measurement in pounds.

6. The method of claim 1, wherein displaying measurement data comprises displaying a measurement in kilograms.

7. The method of claim 1, wherein the handle comprises a non-absorbent material.

8. The method of claim 1, wherein the device is two feet long.

9. The method of claim 1, wherein determining a number of bars to install comprises determining that two bars should be installed.

10. The method of claim 1, wherein determining a number of bars to install comprises determining that three bars should be installed.

11. A method comprising:
   (a) making an incision in the chest of a patient who has been diagnosed with pectus excavatum;
   (b) inserting, via the incision, a device comprising
      (i) a sensor configured to measure force at a face disposed proximate a first end of the device,
      (ii) a handle disposed at a second, opposite end of the device, and
      (iii) a communication interface configured to communicate data based on sensor readings;
   (c) manipulating the device such that the face of the device engages a sternum of the patient;
   (d) communicating, from the device via the communication interface, measurement data based on a reading taken by the sensor during the engagement of the face of the device with the sternum of the patient;
   (e) determining, based on the communicated measurement data, a number of bars to install in the patient's chest; and
   (f) inserting, via one or more incisions, the determined number of bars into the patient's chest in such a manner as to push out the patient's sternum and maintain the patient's sternum in a pushed out condition.

12. The method of claim 11, wherein the step of determining a number of bars to install in the patient's chest comprises determining the number utilizing software configured to do so.

13. The method of claim 11, wherein the sensor comprises a pressure sensor.

14. The method of claim 11, wherein the handle comprises a non-absorbent material.

15. The method of claim 11, wherein the device is two feet long.

16. The method of claim 11, wherein determining a number of bars to install comprises determining that two bars should be installed.

17. The method of claim 11, wherein determining a number of bars to install comprises determining that three bars should be installed.

18. The method of claim 11, wherein the communication interface comprises a wireless communication interface.

19. The method of claim 11, wherein the communication interface comprises a wired communication interface.

20. A method comprising:
   (a) making an incision in the chest of a patient who has been diagnosed with pectus excavatum;
   (b) inserting, via the incision, a device comprising
      (i) a sensor configured to measure force at a face disposed proximate a first end of the device,
      (ii) a handle disposed at a second, opposite end of the device, and
      (iii) an electronic display disposed at the handle;
   (c) manipulating the device such that the face of the device engages a sternum of the patient;
   (d) determining, at the device based on a reading taken by the sensor during the engagement of the face of the device with the sternum of the patient, a number of bars to install in the patient's chest;
   (e) displaying, via the electronic display, the determined number of bars; and
   (f) inserting, via one or more incisions, the determined number of bars into the patient's chest in such a manner as to push out the patient's sternum and maintain the patient's sternum in a pushed out condition.

* * * * *